(12) United States Patent
Kwak et al.

(10) Patent No.: US 8,556,973 B2
(45) Date of Patent: Oct. 15, 2013

(54) INTERVERTEBRAL DISC PROSTHESIS HAVING MULTIPLE BEARING SURFACES

(75) Inventors: Seung Kyu Daniel Kwak, Grafton, MA (US); Amie R. Borgstrom, N. Attleborough, RI (US); Erasmo A. Lopez, Abington, MA (US); John R. Hawkins, Cumberland, RI (US)

(73) Assignee: DePuy Synthes Products, LLC, Raynham, MA (US)

( * ) Notice: Subject to any disclaimer, the term of this patent is extended or adjusted under 35 U.S.C. 154(b) by 1713 days.

(21) Appl. No.: 11/351,710

(22) Filed: Feb. 10, 2006

(65) Prior Publication Data

US 2007/0213821 A1 Sep. 13, 2007

(51) Int. Cl.
*A61F 2/44* (2006.01)

(52) U.S. Cl.
USPC ..................... 623/17.14; 623/17.15

(58) Field of Classification Search
USPC ............ 606/61; 623/17.11–17.16; 403/70, 71
See application file for complete search history.

(56) References Cited

U.S. PATENT DOCUMENTS

| | | | |
|---|---|---|---|
| 3,867,728 A | 2/1975 | Stubstad et al. | |
| 5,562,738 A | 10/1996 | Boyd et al. | |
| 5,683,465 A * | 11/1997 | Shinn et al. | 623/17.14 |
| 5,702,450 A | 12/1997 | Bisserie | |
| 5,893,889 A | 4/1999 | Harrington | |
| 5,928,284 A | 7/1999 | Mehdizadeh | |
| 6,179,874 B1 | 1/2001 | Cauthen | |
| 6,231,609 B1 | 5/2001 | Mehdizadeh | |
| 6,402,785 B1 * | 6/2002 | Zdeblick et al. | 623/17.16 |
| 6,440,168 B1 | 8/2002 | Cauthen | |
| 6,572,653 B1 | 6/2003 | Simonson | |
| 6,679,915 B1 | 1/2004 | Cauthen | |
| 6,692,495 B1 | 2/2004 | Zacouto | |
| 6,743,255 B2 * | 6/2004 | Ferree | 623/17.11 |
| 6,814,737 B2 | 11/2004 | Cauthen | |
| 6,846,328 B2 | 1/2005 | Cauthen | |
| 6,881,228 B2 | 4/2005 | Zdeblick et al. | |
| 7,083,651 B2 * | 8/2006 | Diaz et al. | 623/17.13 |
| 7,195,644 B2 * | 3/2007 | Diaz et al. | 623/17.13 |
| 7,250,060 B2 * | 7/2007 | Trieu | 623/17.15 |
| 2003/0199982 A1 | 10/2003 | Bryan | |
| 2004/0049280 A1 | 3/2004 | Cauthen | |
| 2004/0138749 A1 * | 7/2004 | Zucherman et al. | 623/17.11 |
| 2004/0138753 A1 | 7/2004 | Ferree | |

(Continued)

FOREIGN PATENT DOCUMENTS

| | | |
|---|---|---|
| EP | 0 754 018 | 5/2002 |
| EP | 1 532 948 | 5/2005 |

*Primary Examiner* — Andrew Yang
(74) *Attorney, Agent, or Firm* — Maginot, Moore & Beck LLP

(57) ABSTRACT

An intervertebral disc prosthesis comprises a left prosthesis component and a symmetric right prosthesis component positioned in an intervertebral space. Each prosthesis component includes a superior vertebra facing surface, an inferior vertebra facing surface, and a substantially spherical bearing surface. The bearing surface is positioned between the superior vertebra facing surface and the inferior vertebra facing surface. The superior vertebra facing surface is provided on a superior endplate and the inferior vertebra facing surface is provided on an inferior endplate. The superior endplate is operable to rotate relative to the inferior endplate upon the bearing surface. Each prosthesis component further comprises an elastic member positioned between an endplate and the bearing surface. The elastic member may be substantially cylindrical with a plurality of resilient ribs. Flexion/extension, lateral bending, and torsional movement are allowed by a combination of endplate rotation upon the bearing surface and compression of the elastic member.

10 Claims, 9 Drawing Sheets

(56) References Cited

U.S. PATENT DOCUMENTS

| | | |
|---|---|---|
| 2004/0143270 A1 | 7/2004 | Zucherman et al. |
| 2004/0158254 A1 | 8/2004 | Eiserman |
| 2004/0158328 A1 | 8/2004 | Eisermann |
| 2004/0181284 A1 | 9/2004 | Simonson |
| 2004/0181285 A1 * | 9/2004 | Simonson .................. 623/17.13 |
| 2004/0186577 A1 | 9/2004 | Ferree |
| 2004/0225362 A1 | 11/2004 | Richelsoph |
| 2004/0225363 A1 | 11/2004 | Richelsoph |
| 2004/0225364 A1 | 11/2004 | Richelsoph et al. |
| 2004/0225365 A1 | 11/2004 | Eisermann et al. |
| 2004/0225366 A1 | 11/2004 | Eisermann et al. |
| 2004/0254644 A1 | 12/2004 | Taylor |
| 2004/0267369 A1 | 12/2004 | Lyons et al. |
| 2005/0027364 A1 | 2/2005 | Kim et al. |
| 2005/0033431 A1 | 2/2005 | Gordon et al. |
| 2005/0033432 A1 | 2/2005 | Gordon et al. |
| 2005/0033435 A1 | 2/2005 | Belliard et al. |
| 2005/0033437 A1 | 2/2005 | Bao et al. |
| 2005/0033439 A1 | 2/2005 | Gordon et al. |
| 2005/0043800 A1 | 2/2005 | Paul et al. |
| 2005/0043802 A1 | 2/2005 | Eisermann et al. |
| 2005/0102027 A1 | 5/2005 | Ferree |
| 2005/0102029 A1 | 5/2005 | Blain |
| 2005/0107881 A1 | 5/2005 | Alleyne et al. |
| 2005/0113925 A1 | 5/2005 | Carli |
| 2005/0113926 A1 | 5/2005 | Zucherman et al. |
| 2005/0113928 A1 | 5/2005 | Cragg et al. |
| 2005/0113929 A1 | 5/2005 | Cragg et al. |
| 2005/0125061 A1 | 6/2005 | Zucherman et al. |
| 2005/0125065 A1 | 6/2005 | Zucherman et al. |

* cited by examiner

INTERVERTEBRAL DISC PROSTHESIS HAVING MULTIPLE BEARING SURFACES

BACKGROUND

This invention relates to the field of prosthetics, and more particularly, to an intervertebral disc prosthesis designed to replace a damaged intervertebral disc.

The human spine consists of twenty-four small bones known as vertebrae, or "vertebral bodies," that protect the spinal cord and provide stability to the torso. The vertebrae are arranged in a column and stacked vertically upon each other. Between each vertebra is a fibrous bundle of tissue called an intervertebral disc. These intervertebral discs act as a cushion to the spinal column by absorbing energy and transmitting loads associated with everyday movement. They also prevent the vertebrae from rubbing against each other.

Each intervertebral disc comprises two distinct regions. A firm outer region, the annulus, maintains the shape of the intervertebral disc. An inner region, the nucleus, provides a resilient tissue that enables the disc to function as a shock absorber. Over time, the normal aging process causes the intervertebral discs to degenerate, diminishing their water content and thereby reducing their ability to properly absorb the impact associated with spinal movements. Diminished water content in the intervertebral discs may also cause the vertebrae to move closer together. Tears and scar tissue can weaken the discs, resulting in injury. When the discs wear out or are otherwise injured, a condition known as degenerative disc disease results. With this condition, discs do not function normally and may cause pain and limit activity.

The condition of degenerative disc disease can potentially be relieved by a surgical procedure called artificial disc replacement. In this procedure, the damaged intervertebral disc is replaced by an intervertebral prosthetic device (i.e., an artificial disc).

Many artificial discs have been proposed in the past. A typical prior art artificial disc comprises two metal endplates, one endplate that faces a superior vertebra and one endplate that faces an inferior vertebra. A bearing surface is provided between the two metal endplates, allowing the endplates to rotate relative to one another and generally mimic the motion allowed by a natural disc.

Although current intervertebral disc prosthetic devices have enjoyed success, it would be beneficial to add additional desirable features to the prosthetic devices. For example, the large size of many current intervertebral prosthetic devices requires the devices to be inserted from an anterior approach. An anterior approach presents numerous challenges to the surgeon including the fact that the insertion site may be near the aorta and vena cava. Therefore, it would be advantageous to provide an intervertebral disc prosthesis that is relatively small and includes additional features to facilitate a posterior insertion.

Another advantage would be to provide a prosthetic device that more closely mimics the restricted movements offered by a natural disc. The structure of the human spine generally allows significant degrees of flexion/extension (and particularly flexion) but allows lesser degrees of axial rotation (torsion) and lateral bending. Therefore, it would be advantageous to provide an intervertebral prosthetic device operable to allow a significant degree of flexion/extension in a patient while only allowing restricted axial rotation and lateral bending.

SUMMARY

An intervertebral disc prosthesis is disclosed herein. The intervertebral disc prosthesis is designed for implantation between an upper vertebral body and a lower vertebral body. The intervertebral disc prosthesis generally comprises a left prosthesis component and a symmetric right prosthesis component.

The left prosthesis component includes a left superior vertebra facing surface, a left inferior vertebra facing surface, and a substantially spherical left bearing surface. The left bearing surface is positioned between the left superior vertebra facing surface and the left inferior vertebra facing surface. The left superior vertebra facing surface is provided on a left superior endplate. The left inferior vertebra facing surface is provided on a left inferior endplate. The left superior endplate is operable to rotate relative to the left inferior endplate upon the left bearing surface. The left prosthesis component further comprises a left elastic member positioned between the left superior endplate and the left bearing surface. In an alternative embodiment, the left elastic member may be positioned between the left inferior endplate and the left bearing surface.

The right prosthesis component is generally symmetric with the left prosthesis component. Accordingly, the right prosthesis component includes a right superior vertebra facing surface, a right inferior vertebra facing surface, and a substantially spherical right bearing surface. The right bearing surface is positioned between the right superior vertebra facing surface and the right inferior vertebra facing surface. The right superior vertebra facing surface is provided as part of a right superior endplate. The right inferior vertebra facing surface is provided as part of a right inferior endplate. The right superior endplate is operable to rotate relative to the right inferior endplate upon the right bearing surface. The right prosthesis component further comprises a right elastic member positioned between the right superior endplate and the right bearing surface. In an alternative embodiment, the right elastic member is positioned between the right inferior endplate and the right bearing surface.

The left bearing surface and the right bearing surface are configured such that the center of rotation of the left prosthesis component and right prosthesis component are positioned along a line parallel to a lateral midline of the upper or lower vertebral body when the vertebral bodies are in an equilibrium position. In one embodiment, the center of rotation of each prosthesis component is positioned along a line positioned to the posterior of the lateral midline of each vertebral body.

In one embodiment, the left elastic member and right elastic member are both substantially cylindrical in shape and are both comprised an elastomeric material. The left elastic member and right elastic member both include a plurality of resilient ribs operable to deform when a threshold force is applied to the ribs and return to their original shape when the force is removed. A cavity configured to receive the left elastic member is formed in the left superior plate. A cavity configured to receive the right elastic member is formed in the right superior plate. The left elastic member includes another cavity configured to receive the left bearing surface. The right elastic member includes yet another cavity configured to receive the right bearing surface. In one embodiment the left bearing surface is provided as part of a left dome-shaped member having a concave bearing surface. The right bearing surface is provided as part of a right dome-shaped member having a concave bearing surface. In this embodiment, a left ball-shaped bearing surface is provided on the left inferior endplate and a right ball-shaped bearing member is provided on the right inferior endplate. The left concave bearing surface rotatably engages the left ball-shaped bearing surface. Likewise, the right concave bearing surface rotatably engages the right ball-shaped bearing surface. Thus, a ball and socket arrangement is formed on both the left component and the right component of the intervertebral disc prosthesis.

Flexion/extension movement is primarily allowed in the intervertebral disc prosthesis by rotation of the superior endplates relative to the inferior endplates upon the bearing surfaces. Lateral bending movement to the left or right is primarily allowed by compression of the left elastic member or right elastic member when a force is applied to rotate the superior endplates relative to the inferior endplates. Torsional movement is primarily allowed by compression of the left elastic member and right elastic member when a force is applied to rotate the superior endplates relative to the inferior endplates.

DESCRIPTION

The intervertebral disc prosthesis described herein is comprised of both a first prosthetic device and a complimentary second prosthetic device. The first prosthetic device is first explained herein with the understanding that the second prosthetic device is a symmetric/mirror image of the first device. Arrangement and operation of the first and second prosthetic devices follows the general description of the first prosthetic device.

First Prosthetic Device

Figure 1:
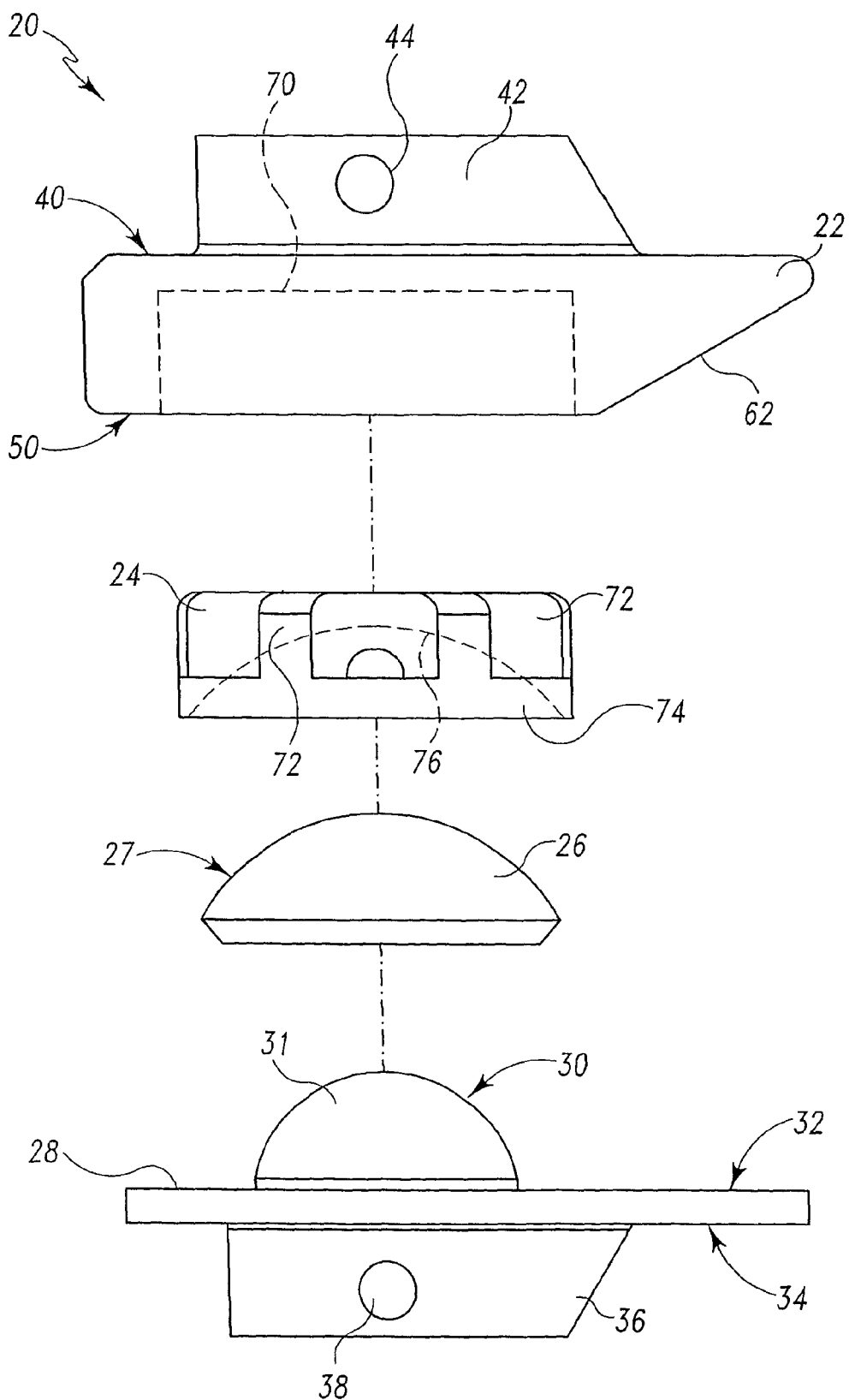
FIG. 1 shows and exploded side view of a first prosthetic device of the intervertebral disc prosthesis.

With general reference to FIG. 1, an exploded side view of a first prosthetic device 20 for an intervertebral disc prosthesis is shown. The first prosthetic device 20 comprises a superior endplate 22, an elastic member 24, a dome-shaped bearing member 26, and an inferior endplate 28. The superior endplate 22 is configured to retain the elastic member 24, and the elastic member 24 is configured to retain the dome-shaped bearing member 26. The dome-shaped bearing member 26 is configured to engage a spherical bearing surface 30 of the inferior endplate 28.

The superior endplate 22 is generally block-shaped with a trapezoidal longitudinal cross-section. The superior endplate 22 is comprised of a rigid material such as a hard metal, ceramic, or hard polymer material. In one embodiment, the superior endplate 22 is comprised of cobalt chromium. In yet another embodiment, the superior endplate 22 is comprised of multiple materials having different properties. For example, the superior endplate 22 may be formed as a multi-durometer elastomer comprising a relatively hard outer portion, a relatively soft inner portion, and a relatively hard bearing portion.

Figure 3:
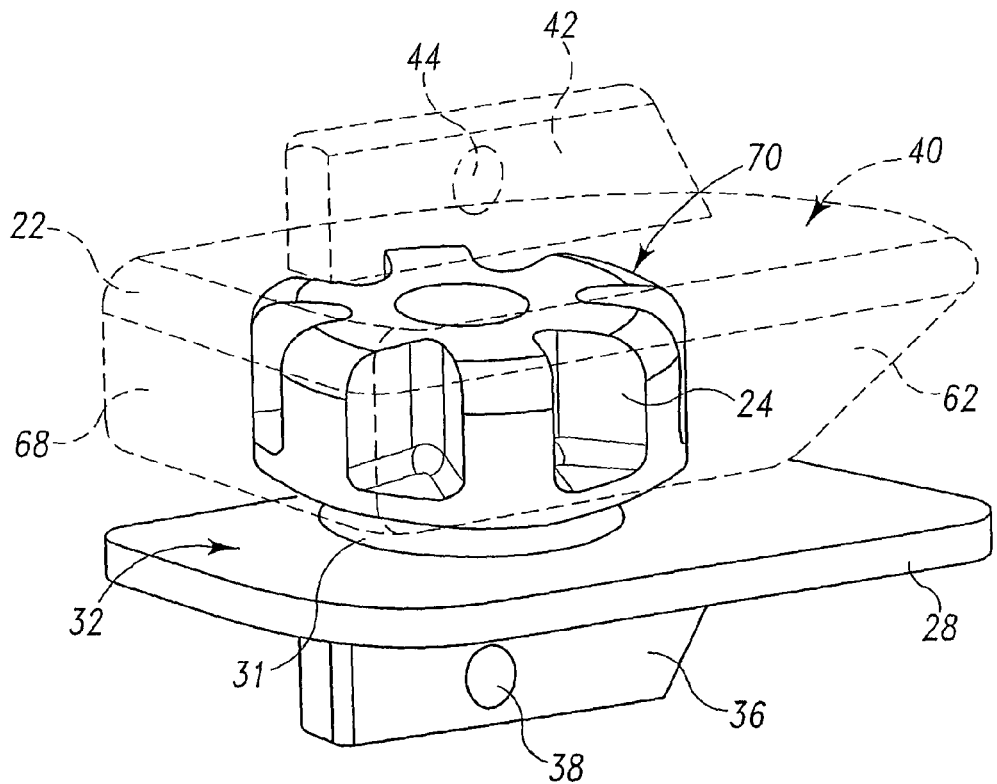
FIG. 3 shows a perspective view of the prosthetic device of FIG. 2 including a view of the elastic member within the superior endplate.

As shown in FIGS. 1 and 3, the superior endplate 22 includes an upper surface 40 designed to face a superior vertebra in an intervertebral space that is defined by the superior vertebra and an inferior vertebra. An upper keel 42 is positioned on the upper surface 40 and extends from the upper surface. The keel 42 is configured to fit in a channel formed in the superior vertebra and secure the endplate 22 to the superior vertebra. An alignment hole 44 is provided in the keel 42. As will be explained in further detail below, the alignment hole 42 is designed to assist the surgeon in aligning the first prosthetic device 20 with a second prosthetic device.

Figure 4:
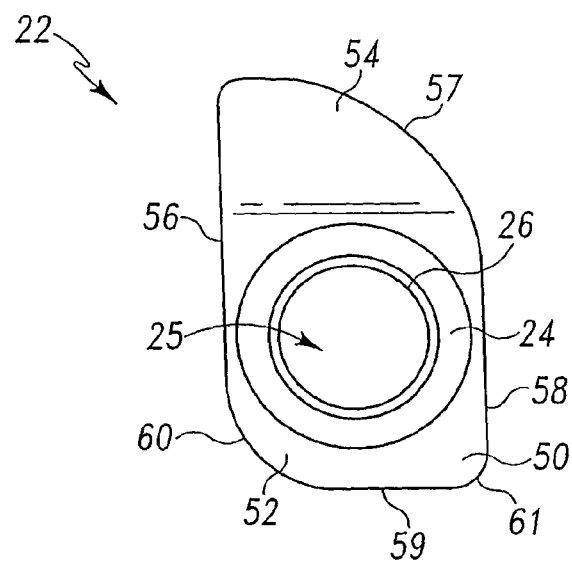
FIG. 4 shows a bottom view of the superior plate of the prosthetic device of FIG. 1.

With reference now to FIG. 4, the superior endplate 22 also includes a lower surface 50. The lower surface 50 includes a posterior lower tier 52 and an anterior sloped portion 54. The anterior sloped portion 54 ramps upward from the lower tier 52 at an angle. In one embodiment, the angle between the lower tier 52 and the sloped portion 54 is about 30°. The perimeter of the lower surface 50 defines a right edge 56 that is generally parallel to a left edge 58, with the right edge being longer than the left edge. A curved anterior edge 57 extends between the right edge 56 and left edge 58. The curved anterior edge 57 begins to curve away from the left edge 58 at the lower tier 52 and gradually ramps upward along with the sloped portion 54 as it moves toward the right edge 56. A posterior edge 59 is substantially perpendicular to the right edge 56 and left edge 58. The posterior edge 59 extends between the right edge 56 and left edge 58 along curved corner portions 60 and 61 of the lower tier 52. In one alternative embodiment, the posterior edge comprises a sloped portion, similar to the anterior sloped portion 54.

Figure 2:
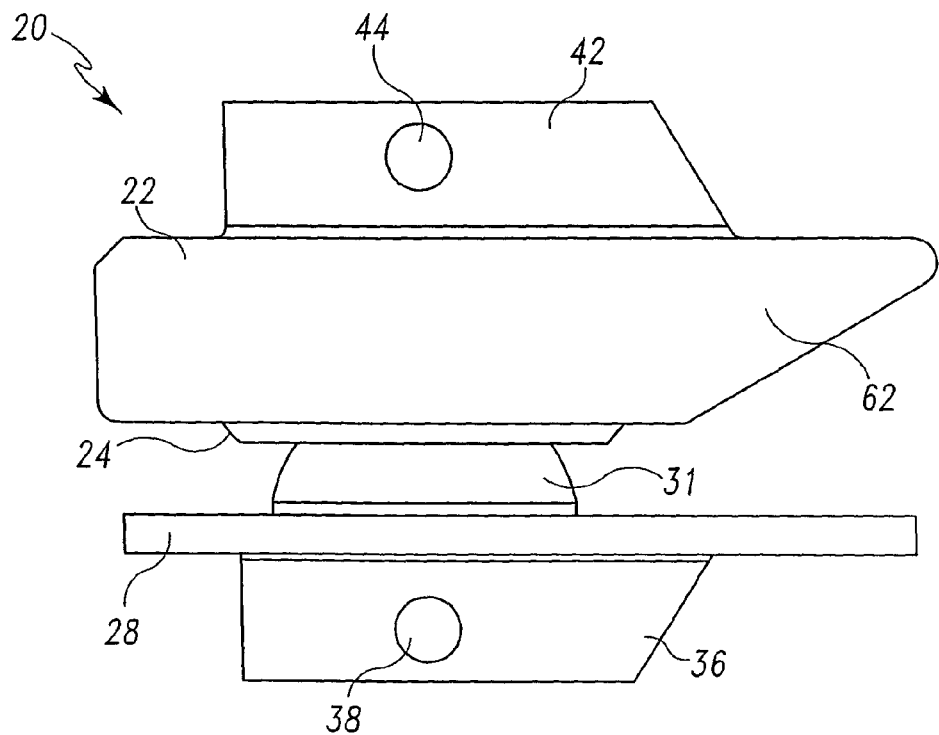
FIG. 2 shows a side view of the assembled prosthetic device of FIG. 1.
Figure 6:
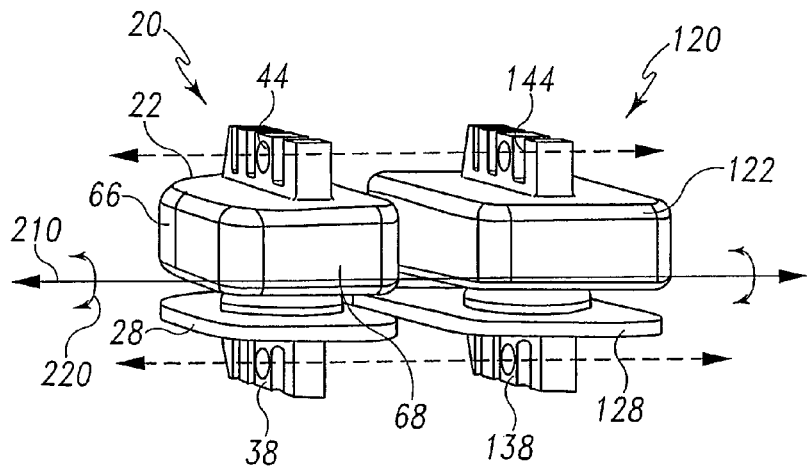
FIG. 6 shows a rear perspective view of the first and second prosthetic devices as arranged in FIG. 5.
Figure 7:
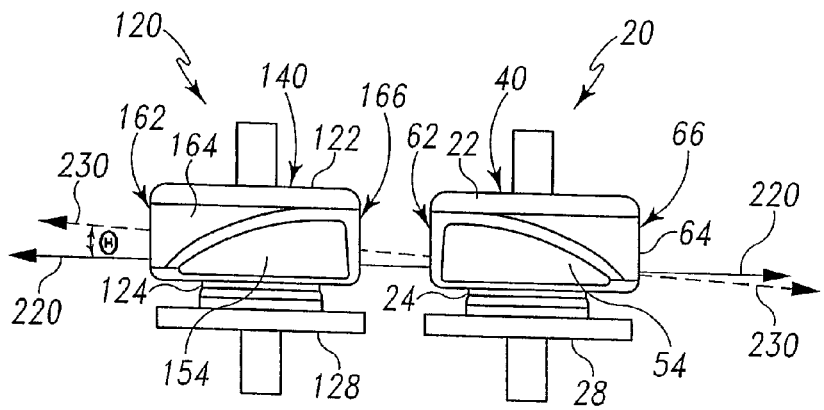
FIG. 7 shows a front view of the intervertebral disc prosthesis of FIG. 6.

Sidewalls 62, 64, 66 and 68 define the sides of the superior plate 22 and extend between the upper surface 40 and lower surface 50. The right sidewall 62 is best seen in FIGS. 1-3, the left sidewall 66 and posterior sidewall 68 are best seen in FIG. 6, and the anterior sidewall 64 is best seen in FIG. 7. Along with the upper surface 40 and lower surface 50, the sidewalls 62, 64, 66, and 68 define the shape and volume of the superior endplate 22.

As noted by the dotted lines in FIG. 1 associated with the superior endplate 22, a cylindrical cavity 70 is formed in the superior endplate 22. The cavity 70 provides a generally cylindrical hole in the superior endplate 22. An opening to the cavity 70 is formed in the lower surface 50 of the superior endplate 22. The elastic member 24 is designed to fit within the cavity 70 as shown in FIGS. 3 and 4. The elastic member 24 may be secured in the cavity 70 in numerous ways such as mechanically fastened in the cavity, friction fit in the cavity, or bonded within the cavity. For example, an adhesive material may be used to secure the elastic member 24 within the cavity 70. Alternatively, a chemical bond may be formed between the superior plate 22 and the elastic member 24.

The elastic member 24 is designed to provide a resilient cushion between the superior endplate 22 and the inferior endplate 28 while also allowing some limited movements between the endplates 22 and 28. The elastic member 24 disclosed herein is generally cylindrical in shape. The elastic member is formed from an elastomeric material having resilient qualities. For example, in one embodiment, the elastic member 24 may be comprised of polyurethane. As another example, the elastic member 24 may be comprised of silicone.

The elastic member 24 includes a lower disc portion 74 and an upper rib portion. The upper rib portion includes six equally spaced ribs 72 that extend from a central axis of the elastic member 24. Void spaces are provided between the ribs 72. Each rib 72 may be deformed when exposed to a threshold force. For example, when a force is applied to a rib 72 it may bend into the void space provided next to the rib. When the force is removed, the ribs resiliently move back to their original shape.

As shown by the dotted line on the elastic member 24 of FIG. 1, a domed cavity 76 is formed in the elastic member 24. The opening to the domed cavity 76 is provided on the bottom portion of the elastic member 24. The domed cavity 76 is designed to receive the dome-shaped bearing member 26. The dome-shaped bearing member 26 is secured within the cavity 76 of the elastic member 24 using any of numerous means known in the art. For example, a mechanical fastener may be used to secure the bearing member in the cavity 76 or an adhesive may be used to bond the bearing member 26 in the cavity 76. Alternatively, a chemical bond may be formed between the elastic member 24 and the dome-shaped bearing member 26.

The dome-shaped bearing member 26 is comprised of a wear-resistant material such as a metal, ceramic or a hardened polymer. In one embodiment, the bearing 26 is comprised of cobalt chromium. The dome-shaped bearing 26 is generally spherical in shape and includes a convex upper surface 27 and a concave lower surface 25 (see FIG. 4). The convex upper surface 27 is designed to fit within the cavity 76 of the elastic member 24. A fastener or bond may be used to secure the bearing 26 to the elastic member 24. The concave lower surface 25 of the bearing 26 is configured to be congruent with and rotatably engage a ball-shaped bearing 31 provided on the inferior endplate 28. Because the dome-shaped bearing 26 is secured to the elastic member 24 which, in turn, is secured to the superior plate 22, the dome-shaped bearing 26 provides a bearing surface for rotation of the superior plate 22 relative to the inferior plate 28.

With continued reference to FIG. 1, the inferior plate 28 is comprised of a rigid material such as a rigid metal, ceramic or a rigid polymer. The inferior plate may comprise a single molded piece or a multi-piece component. In one embodiment, the inferior plate comprises a substantially flat upper surface 32 with a ball-shaped bearing 31 formed on the upper surface 32. The ball-shaped bearing 31 is centrally positioned upon the upper surface 32 slightly posterior of a lateral midline. The ball-shaped bearing 31 provides a substantially spherical bearing surface 30 designed and dimensioned to rotatably engage the concave lower surface 25 of the dome-shaped bearing 26. The concave lower surface 25 of the dome-shaped bearing 26 essentially provides a socket for the spherical bearing surface 30, resulting in a ball and socket arrangement between the superior endplate 22 and the inferior endplate 28.

The center of the bearing 31 defines a center of rotation for the first prosthetic device 20. In particular, with the superior endplate 22 positioned on the inferior endplate 28 and the spherical bearing surface 30 engaging the convex lower surface of the dome-shaped bearing 26, the superior plate 22 is adapted to rotate about the center of the bearing 31. Thus, the spherical bearing surface 30 and the dome-shaped bearing 26 form an articulating joint, and particularly a ball and socket joint, between the superior plate 22 and the inferior plate 28.

The inferior plate 28 further comprises a lower surface 34 designed to face the inferior vertebra of the intervertebral space. A lower keel 36 is positioned on the lower surface 34 and extends below the lower surface 34. The keel 36 is configured to fit in a channel formed in an inferior vertebra and secure the inferior endplate 28 to the inferior vertebra. An alignment hole 38 is provided in the keel 36. As will be explained in further detail below, the alignment hole 38 is designed to assist the surgeon in aligning the first prosthetic device 20 with a second prosthetic device. In an alternative embodiment, teeth are provided on the endplate surfaces in place of the upper and lower keel. Such teeth may be used for fixing the endplates on the vertebral bodies and may also be used to assist in proper alignment of the endplates.

Arrangement of First and Second Prosthetic Devices

As stated above, the first prosthetic device 20 is configured for use with a complimentary second prosthetic device 120. The second prosthetic device is a mirror image of the first prosthetic device shown in FIGS. 1-4. The first and second prosthetic devices 20 and 120 are designed for side-by-side arrangement within an intervertebral space. Such a side-by-side arrangement is now described with reference to FIGS. 5-7.

Figure 5:
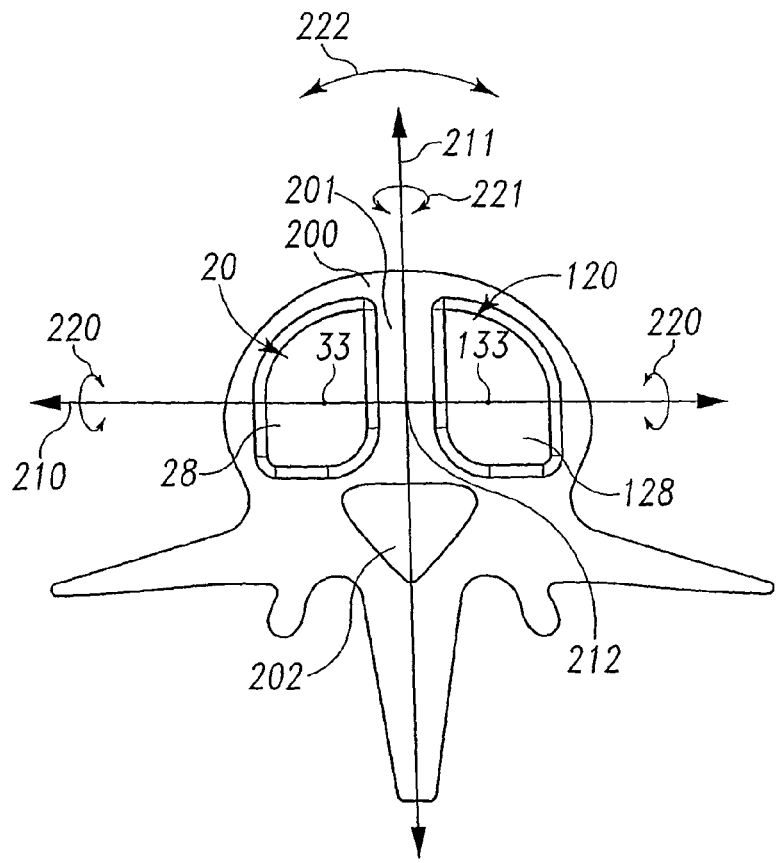
FIG. 5 shows the arrangement of the prosthetic device of FIG. 1 and a second complementary prosthetic device in relation to a vertebral body.

FIG. 5 shows the footprint of the inferior endplate 28 of the first prosthetic device 20 positioned on the left side of an inferior vertebral body 200. The inferior endplate 128 of the second complimentary prosthetic device 120 is positioned on the right side of the vertebral body 200. The vertebral body 200 includes a disc region 201, a spinal foramen 202, and a plurality of facet joints. A lateral midline of the vertebral body 200 is shown by line 210. The lateral midline 210 is line that extends from left to right across the vertebral body and is perpendicular to a longitudinal center line 211 extending between an extreme anterior position and an extreme posterior position on the vertebral body. While the lateral midline 210 is intended to extend through a center of the disc region 201, it should be understood that numerous lines extending from left to right through a central point of the disc region 210 may be considered lateral midlines. For example, in one embodiment, the lateral midline is a line slightly to the posterior of the actual center of the disc region 201.

As suggested by the footprints of the inferior endplates 28 and 128 upon the vertebral body 200 in FIG. 5, the first prosthetic device 20 and second prosthetic device 120 are symmetrically aligned upon the vertebral body 200 about the longitudinal center line 211. Furthermore, the center of rotation 33 of the first prosthetic device 20 is aligned with the center of rotation 133 of the complimentary second prosthetic device 120 along the lateral midline 210 or slightly posterior to the lateral midline 210 of the vertebral bodies. The centers of rotation 33 and 133 are shown in FIG. 5 projected on to the vertebral body. Because the intervertebral disc prosthesis is a two-piece component with a left prosthesis device 20 and a right prosthesis device 120, the prosthesis can be easily implanted in a patient from a posterior approach. In particular, the left prosthesis device 20 may be inserted from the left side of the spinal cord 202 and the right prosthesis device 120 may be inserted from the right side of the spinal cord 202. During the implantation procedure, it may be necessary to remove facet joints to facilitate the posterior approach. While facet joints limit the degree of torsional movement, the intervertebral disc prosthesis described herein also limits torsional movement, as will be discussed in further detail below. Therefore, complications resulting from removed facet joints are compensated by the intervertebral disc prosthesis described herein. However, in some circumstances it may be desirable to use stabilizer devices on the facet joints to further limit the amount of torsional movement.

FIG. 6 provides a rear perspective view of the first prosthetic device 20 aligned next to the complimentary second prosthetic device 120. As shown in FIG. 6, the alignment hole 44 in the upper keel of the first prosthetic device 20 is aligned with the alignment hole 144 of the second prosthetic device 120. Similarly, the alignment hole 38 of the lower keel of the first prosthetic device 20 is aligned with the alignment hole 138 of the lower keel of the second prosthetic device. During implantation of the first and second prosthetic devices, the surgeon may advantageously use the alignment holes to confirm precise alignment of the first prosthetic device 20 relative to the second prosthetic device. In particular, a lateral x-ray image of the first and second prosthetic devices during the implantation procedure should reveal holes 38 and 138 in alignment along a lateral midline and a similar alignment between holes 44 and 144.

FIG. 7 provides a front view of the first prosthetic device 20 positioned side-by-side with the second prosthetic device 120. As shown in FIG. 7 (and considering FIG. 4), the anterior sidewall 64 of the first superior endplate 22 curves around and upward from the left sidewall 66 and tapers into the junction of the right sidewall 62 and the upper surface 40 of the endplate 22 at an extreme forward position of the endplate. Similarly, the anterior sidewall 164 of the second superior endplate 122 curves around and upward from the left sidewall 162 and tapers into the junction of the right sidewall 166 and the upper surface 140 of the endplate 122 at an extreme forward position of the endplate. In each case the anterior sloped portion 54 and 154 of the lower surface of the endplate can be seen from the front view.

Figure 8:
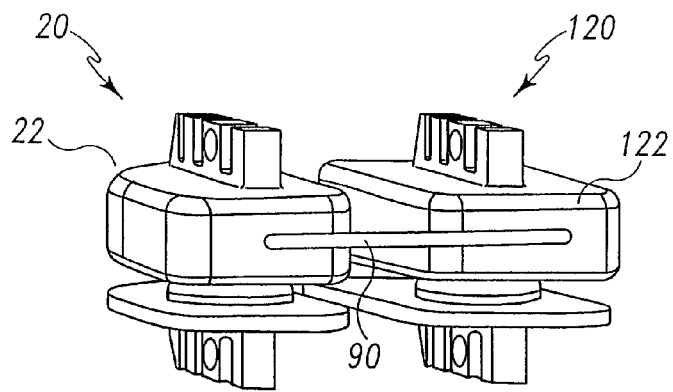
FIG. 8 shows an alternative embodiment of the intervertebral disc prosthesis of FIG. 6.

With reference to FIG. 8, in one embodiment, the first prosthetic device 20 and second prosthetic device 120 include a connecting member spanning between the first prosthetic device and the second prosthetic device. For example, as shown in FIG. 8, a connection rod 90 may extend between the first superior plate 22 and the second superior plate 122. This connection rod 90 joins the first superior plate 22 to the second superior plate 122, insuring that the first superior plate 22 remains aligned with the second superior plate 122 and move in unison as a single rigid component. In particular, the connection rod 90 prohibits drifting of one endplate relative to the other following implantation of the endplates in the patient.

Prosthesis Movement

When the first prosthetic device 20 and second prosthetic device 120 are implanted in an intervertebral space, the intervertebral disc prosthesis generally allows a significant degree of flexion/extension movement but a lesser degree of torsional and lateral bending movement. With reference to FIGS. 5-7, flexion/extension movement is represented by arrows 220 about lateral midline 210. Because superior endplates 22 and 122 are both secured to the same superior vertebral body, they will move in unison. Likewise, inferior endplates 28 and 128 are secured to the same inferior vertebral body and will move in unison. The center of rotation for each prosthetic device is provided along line 210, which is the line about which flexion and extension occur. Accordingly, significant degrees of flexion and extension are provided as indicated by arrow 220 about line 210 as the center of rotation of both the first prosthetic device 20 and the second prosthetic device 120 are positioned along line 210. Extension is limited to a degree at which the superior plates 22 and 122 rotate posteriorly into contact with the inferior plates 28 and 128. Likewise, flexion is limited to a degree at which the superior plates 22 and 122 rotate anteriorly into contact with the inferior plates 28 and 128. It should be noted that substantially more flexion is allowed than extension because of the anterior sloped portions 54 and 154 on the superior plates 22 and 122 which provide additional clearance between the superior plates 22 and 122 and the inferior plates 28 and 128 during anterior rotation of the plates. In one embodiment, allowed degrees of extension may be as much as 5° or 10° while allowed degrees of flexion may be as much as 10° or 20°.

The intervertebral disc prosthesis also allows some degree of lateral bending as noted by arrow 221 in FIG. 5 indicating rotation about longitudinal center line 211. The degree of lateral bending is substantially dependent upon the deformation properties of the elastic members 24 and 124 of the respective prosthetic devices 20 and 120. In particular, during lateral bending the superior vertebra and inferior vertebra attempt to rotate about longitudinal center line 211 of FIG. 5. However, because centers of rotation 33 and 133 are removed from the longitudinal center line 211, these points act as supports that generally resist lateral bending. Nevertheless, some degree of lateral bending is possible due to the deformation properties of the elastic members 24 and 124. For example, as shown in FIG. 7 dotted line 230 indicates a degree $\theta$ of leftward lateral bending from the equilibrium position indicated by line 220. During this degree of leftward lateral bending, the elastic member 24 in the left prosthesis device 20 is compressed as the left superior endplate 22 rotates relative to the left inferior endplate 28. In addition to compression of the elastic member, a small amount of pivoting may occur between the left bearing surfaces 25 and 30. If the leftward lateral bending force is large enough, the bearing surface retained in the right superior endplate 122 may actually disengage and pull away from the ball bearing of the right inferior endplate 128. Of course, the bearing surfaces return to full engagement following removal of such force. Accordingly, the intervertebral disc prosthesis described herein provides for relatively limited degrees of lateral bending movement. In one embodiment, lateral bending as represented by angle $\theta$ in FIG. 7 is generally limited to a range from 2° to 6°.

In addition to the movements described above, the intervertebral disc prosthesis also allows a limited amount of axial rotation (torsional) movement, as indicated by arrow 222 in FIG. 5. Arrow 222 suggests some movement about an axis 212 that is perpendicular to axes 210 and 211. However, rotation in this torsional direction 222 is limited as the first prosthetic device 20 and the second prosthetic device 120 provide two fixed points on axis 210, as noted by centers of rotation 33 and 133 in FIG. 5. Therefore, the only torsional movement of the superior endplates 22 and 122 relative to the inferior endplates 28 and 128 results from compression of the elastic members 24 and 124 between the plates. For example, during torsional movement to the left, the anterior portion of left elastic member 24 is compressed, while the posterior portion of right elastic member 124 is compressed. The degree of axial rotation allowed is dictated by the deformation properties of the elastic members 24 and 124 and the force imposed upon the elastic members. In one embodiment, the degree of axial rotation is limited to a range from 1° to 3°.

Alternative Embodiment

With reference now to FIGS. 9-13, an alternative embodiment of a prosthetic device 300 is shown. Similar to the prosthetic devices described above, the prosthetic device 300 is designed for use as one side of a two-component intervertebral disc prosthesis.

With general reference to FIGS. 9-12, an exploded side view of a right side first prosthetic device 320 for an intervertebral disc prosthesis 300 is shown. The first prosthetic device 320 comprises a superior endplate 322, an elastic member 324, a dome-shaped bearing member 326, and an inferior endplate 328. The superior endplate 322 is configured to retain the elastic member 324, and the elastic member 324 is configured to retain the dome-shaped bearing member 326. The dome-shaped bearing member 326 is configured to engage a spherical bearing surface 330 of the inferior endplate 328.

Figure 9:
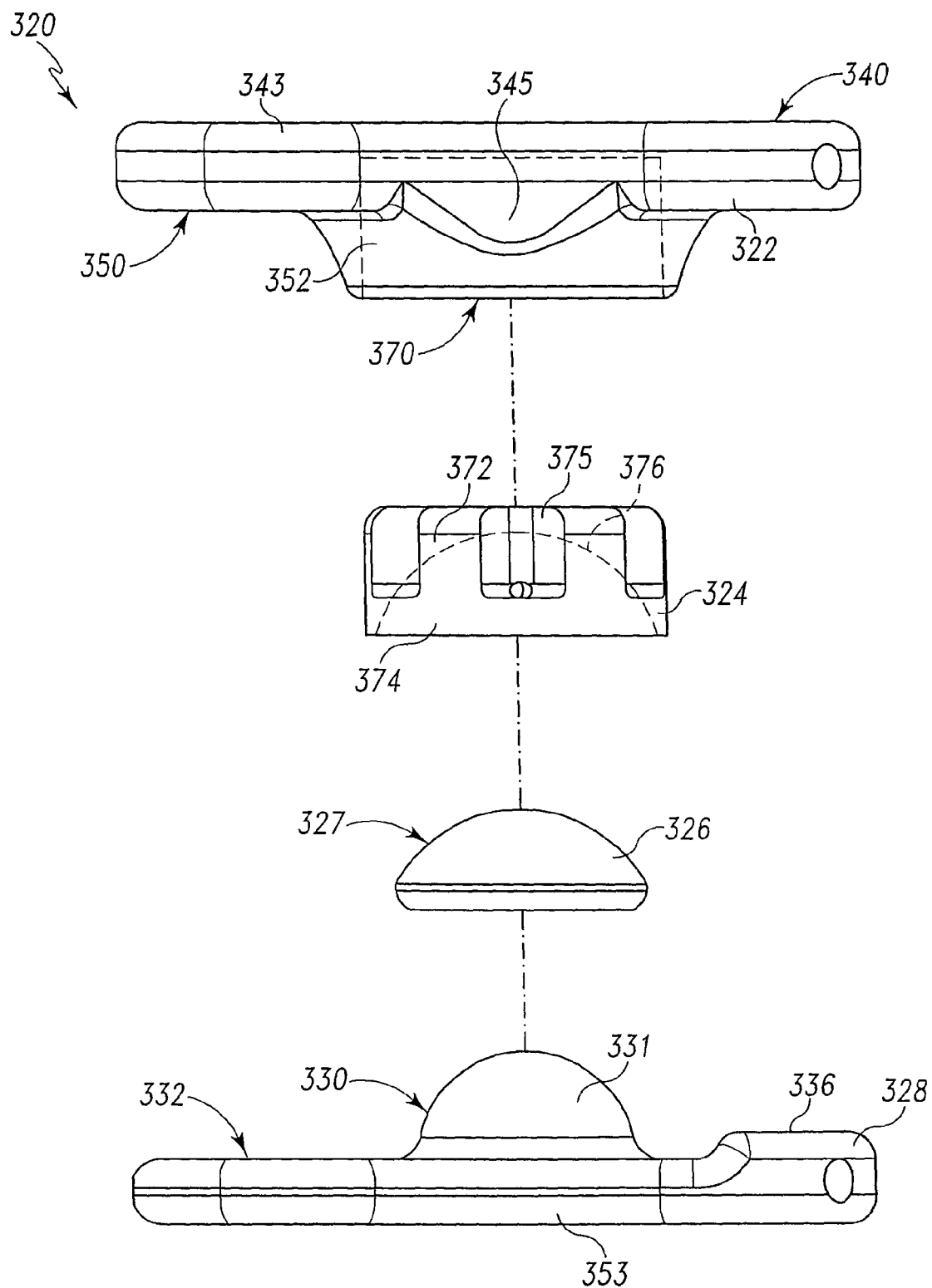
FIG. 9 shows an exploded side view of an alternative embodiment of the prosthetic device of FIG. 1.
Figure 10:
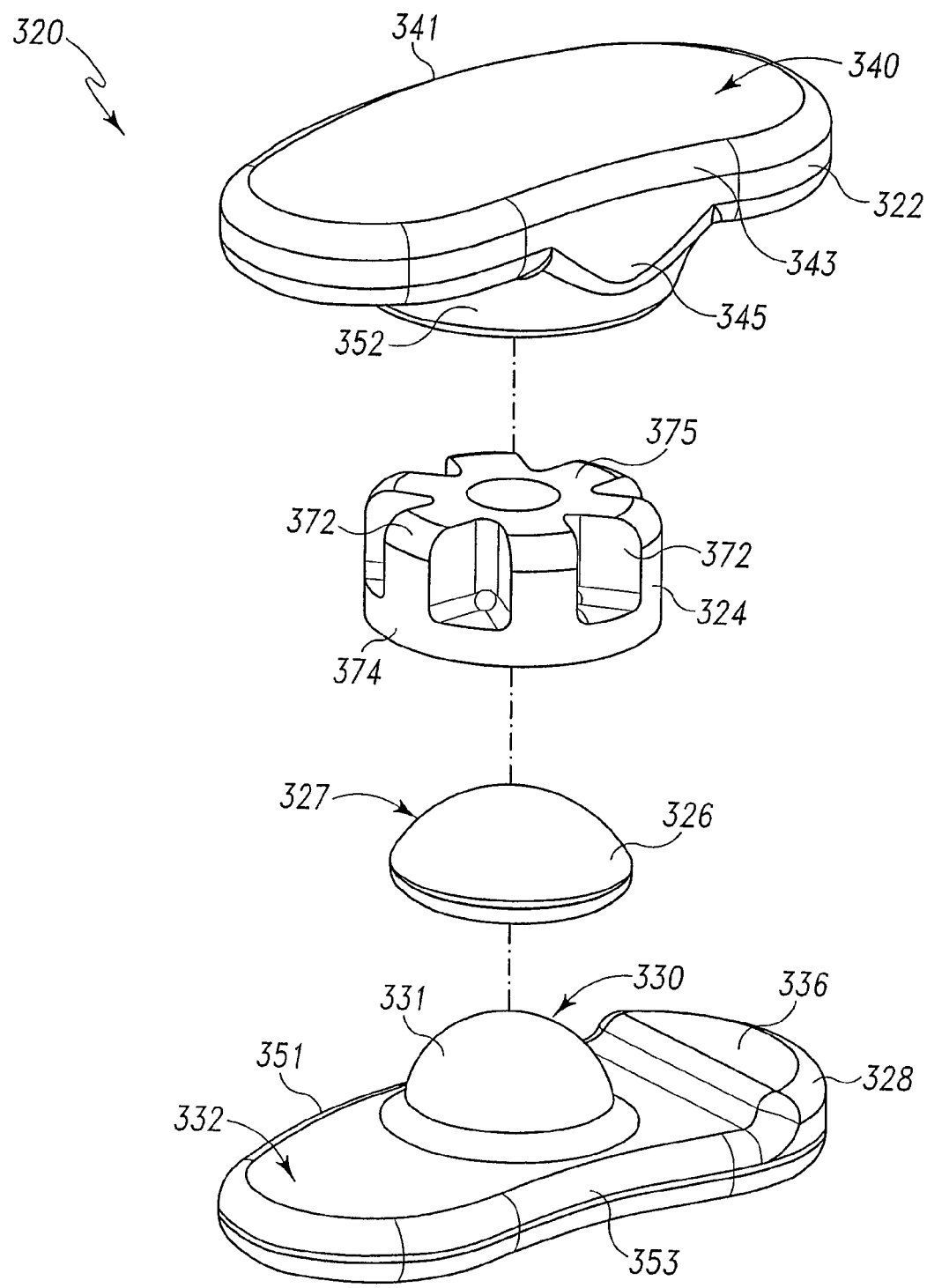
FIG. 10 shows an exploded anterior perspective view of the prosthetic device of FIG. 9.
Figure 11:
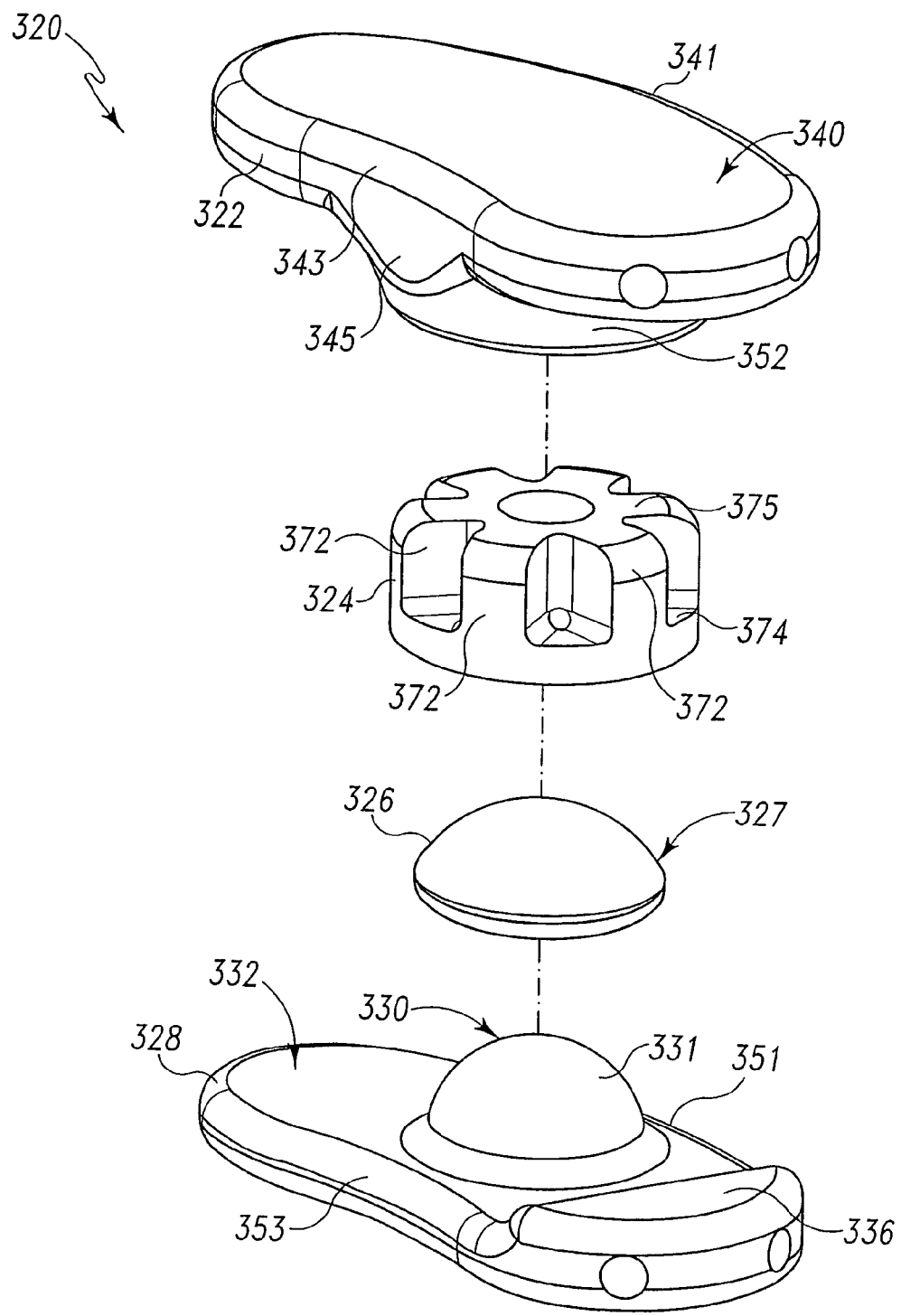
FIG. 11 shows an exploded posterior perspective view of the prosthetic device of FIG. 9.
Figure 12:
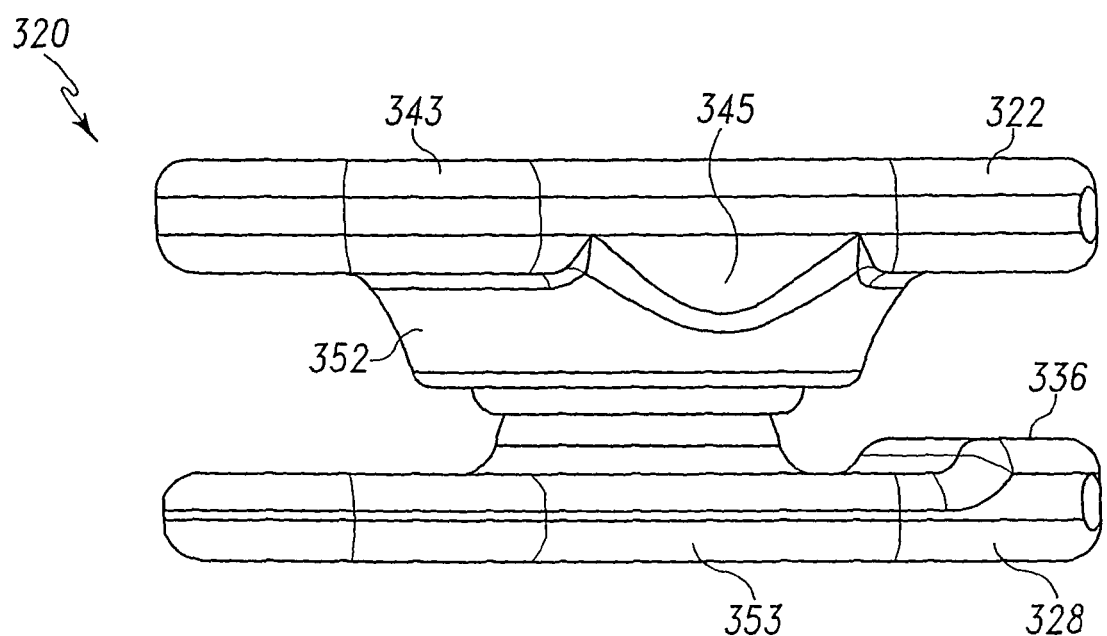
FIG. 12 shows a side view of the assembled prosthetic device of FIG. 9.

As shown in FIGS. 9-11, the superior endplate 322 includes an upper surface 340 designed to face a superior vertebra in an intervertebral space. While not shown in the figures, fixation devices such as teeth or a keel may be used to secure the superior endplate 322 to the superior vertebra. The footprint of the superior endplate 322 is generally kidney-shaped with a generally convex curvature on the right perimeter 341 and a generally concave curvature along the left perimeter 343. A tab 345 extends downward from the left perimeter 343.

The superior endplate 322 also includes a lower surface 350 opposite the upper surface 340. The lower surface 350 includes a circular mouth 352 that defines a cavity 370 designed to receive the elastic member 324. The mouth 352 comprises a frusto-conical sidewall that extends downward to an opening to the cavity 370. The elastic member 324 is designed to fit within the cavity 370. The elastic member 324 may be secured in the cavity in numerous ways such as mechanical fasteners, snap-fit, or bonded within the cavity.

The elastic member 324 is designed to provide a resilient cushion between the superior endplate 322 and the inferior endplate 328 while allowing some limited movements between the endplates 322 and 328. The elastic member 324 is generally cylindrical in shape and is formed from an elastomeric material having resilient qualities. The elastic member 324 includes a lower disc portion 374 and an upper rib portion 375. The upper rib portion 375 includes six equally spaced ribs 372 that extend from a central axis of the elastic member 324. Each rib 372 may be deformed when exposed to a threshold force. When the force is removed, the ribs 372 resiliently move back to their original shape.

As shown by the dotted line on the elastic member 324 of FIG. 9, a domed cavity 376 is formed in the elastic member 324. The opening to the domed cavity 376 is provided on the bottom portion 374 of the elastic member 324. The domed cavity 376 is designed to receive the dome-shaped bearing member 326. The dome-shaped bearing member 326 is secured within the cavity 376 of the elastic member 324 using a fastener or other means such as a bond.

The dome-shaped bearing member 326 is comprised of a wear-resistant material such as a metal, ceramic or a hardened polymer. The dome-shaped bearing 326 is generally spherical in shape and includes a convex upper surface 327 and a concave lower surface (not shown). The convex upper surface 327 is designed to fit within the cavity 376 of the elastic member 324. A fastener, bond or other means may be used to secure the bearing 326 to the elastic member 324. The concave lower surface of the bearing 326 is configured to be congruent with and rotatably engage a spherical bearing surface 330 provided on the inferior endplate 328. Because the dome-shaped bearing 326 is secured to the elastic member 324 which, in turn, is secured to the superior plate 322, the dome-shaped bearing 326 provides a bearing surface for rotation of the superior plate 322 relative to the inferior plate 328.

With continued reference to FIGS. 9-12, the inferior plate 328 is formed of a rigid material such as a rigid metal, ceramic or a rigid polymer. The inferior plate 328 comprises a substantially flat upper surface 332 with a ball-shaped bearing 331 formed on the upper surface 332. The ball-shaped bearing 331 is centrally positioned upon the upper surface 332 slightly posterior of a lateral midline. The ball-shaped bearing 331 provides a substantially spherical bearing surface 330 designed and dimensioned to rotatably engage the concave lower surface of the dome-shaped bearing 326. The concave lower surface of the dome-shaped bearing 326 essentially provides a socket for the spherical bearing surface 330, resulting in a ball and socket arrangement between the superior endplate 322 and the inferior endplate 328.

The center point of the bearing 331 defines a center of rotation for the first prosthetic device 320. In particular, with the superior endplate 322 positioned on the inferior endplate 328 and the spherical bearing surface 330 engaging the convex lower surface of the dome-shaped bearing 326, the superior plate 322 is adapted to rotate relative to the inferior plate 328 about the center of rotation.

Also included on the upper surface 332 of the inferior endplate 328 is a posterior upper tier 336. The posterior upper tier 336 provides a surface that restricts the degree of extension available to the superior plate 322 relative to the inferior plate 328.

The inferior plate 328 further comprises a lower surface 334 designed to face the inferior vertebra of the intervertebral space. While not shown in the figures, fixation devices such as teeth or a keel may be used to secure the inferior endplate 328 to the inferior vertebra. The footprint of the inferior endplate 328 is generally kidney-shaped with a generally convex curvature on the right perimeter 351 and a generally concave curvature along the left perimeter 353.

Figure 13:
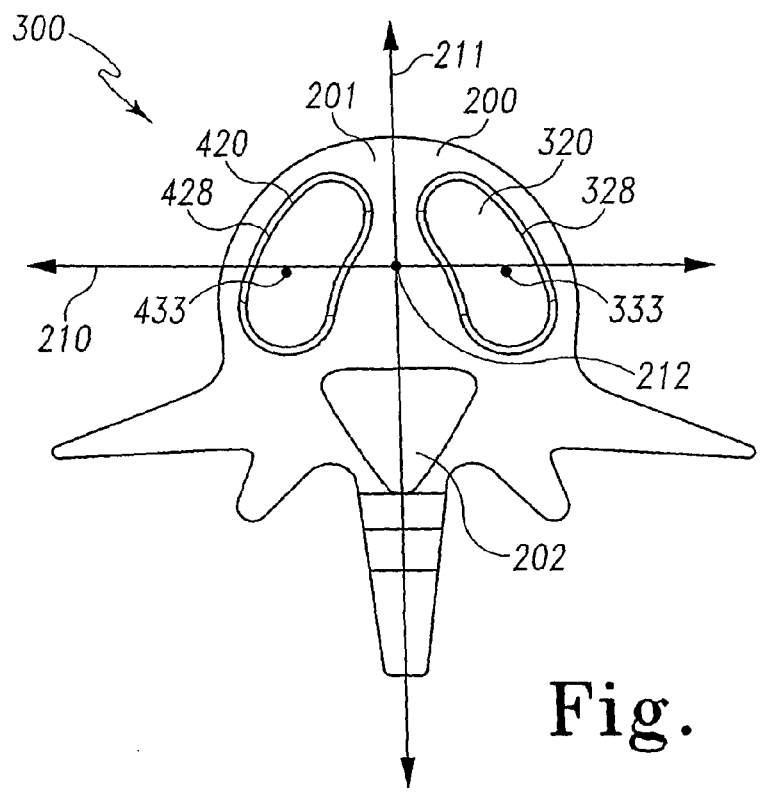
FIG. 13 shows the arrangement of the prosthetic device of FIG. 9 and a second complementary prosthetic device in relation to a vertebral body.

As stated previously, the first prosthetic device 320 is configured for use with a complimentary second prosthetic device 420. The second prosthetic device 420 is a mirror image of the first prosthetic device shown in FIGS. 9-12. The first and second prosthetic devices 320 and 420 are designed for side-by-side arrangement within an intervertebral space. FIG. 13 shows the footprint of the inferior endplate 328 of the first prosthetic device 320 positioned on the right side of an inferior vertebral body 200. The inferior endplate 428 of the second complimentary prosthetic device 420 is positioned on the left side of the vertebral body 200. The vertebral body 200 includes a disc region 201, a spinal foramen 202, and a plurality of facets. A lateral midline of the vertebral body 200 is shown by line 210.

As suggested by the footprints of the endplates 328 and 428 upon the vertebral body 200 in FIG. 13, the first prosthetic device 320 and second prosthetic device 420 are symmetrically aligned upon the vertebral body 200 about the longitudinal center line 211. Furthermore, the center of rotation 333 of the first prosthesis 320 is aligned with the center of rotation 433 of the complimentary second prosthesis 420 along the lateral midline 210. Because the intervertebral disc prosthesis is a two-piece component with a right prosthesis device 320 and a left prosthesis device 420, the prosthesis can be easily implanted in a patient from a posterior approach. Furthermore, as explained previously, the intervertebral disc prosthesis allows significant degrees of flexion/extension movement, but substantially limited degrees of lateral bending and torsional movement.

In an alternative configuration not shown in the figures, the first prosthetic device 320 and the second prosthetic device 420 include a connection member, such as additional bars or other links joining the first prosthetic device and the second prosthetic device, similar to the arrangement shown in FIG. 8. For example, two superior endplates of the first prosthetic device 320 and the second prosthetic device 420 may be rigidly connected and fixed to one another such that movement of one endplate causes movement of the other endplate. Therefore, the superior endplates may form a single rigid body and the inferior endplates may form a single rigid body.

Figure 14:
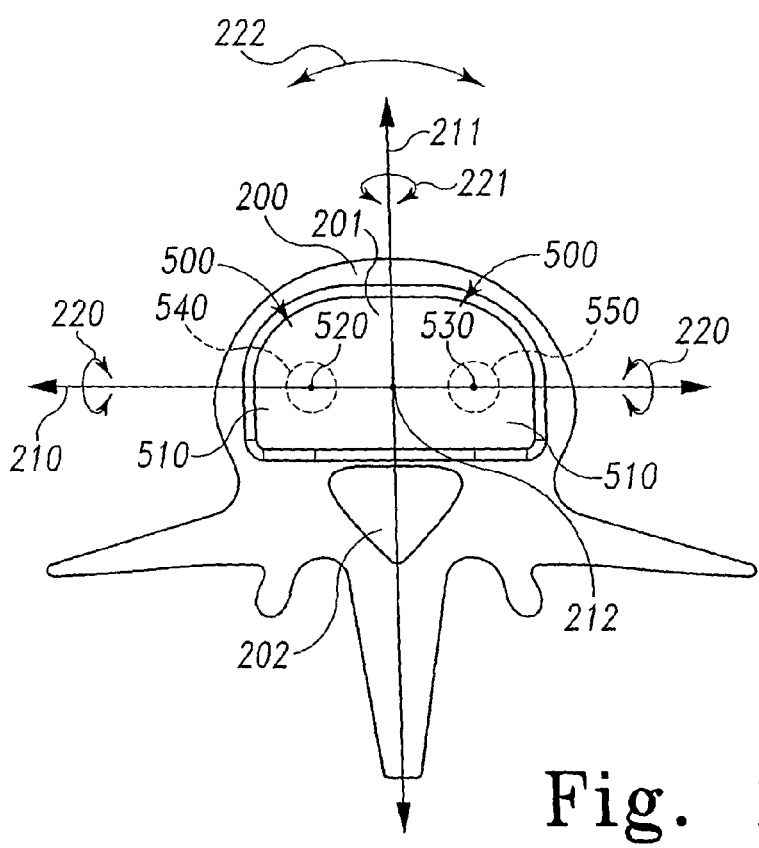
FIG. 14 shows an alternative embodiment of the intervertebral disc prosthesis of FIG. 1 in relation to a vertebral body.

Another alternative configuration shown in FIG. 14. In this embodiment, the intervertebral disc prosthesis 500 comprises a single superior plate 510 and a single inferior plate (not shown) with multiple articulating joints positioned between the superior plate 510 and the inferior plate. The articulating joints are particularly a first ball and socket joint and a second ball and socket joint. The first ball and socket joint defines a first center of rotation 520 and the second ball and socket joint defines a second center of rotation 530. The first center of rotation 520 and the second center of rotation 530 are shown projected on the superior plate 510 in FIG. 14 and are provided along a line substantially parallel to the lateral midline 210. To facilitate the first ball and socket joint and the second ball and socket joint, a first socket and a second socket are both provided in the superior plate 510, as suggested by circular dotted lines 540 and 550 in FIG. 14. Similarly, the inferior endplate includes a first ball bearing and a second ball bearing positioned which define the first center of rotation and the second center of rotation for the prosthesis 500. An elastomer, such as elastic member 24 described above is provided between the superior endplate and the inferior endplate in a similar fashion to that described above. The prosthesis 500 is designed for insertion in the patient using either a lateral approach or an anterior approach.

Although the present invention has been described with respect to certain preferred embodiments, it will be appreciated by those of skill in the art that other implementations and adaptations are possible. For example, the elastic member could be positioned between the inferior endplate and the spherical bearing surface rather than between the superior endplate and the dome-shaped bearing surface. Also, the elastic member could be positioned between both the superior endplate and the dome-shaped bearing surface and the inferior endplate and the spherical bearing surface. In such embodiments, the inferior endplate may include a cavity to receive the elastic member configured for connection to the spherical bearing surface. As another example of an alternative embodiment, the spherical bearing surface may be positioned on the superior endplate rather than the inferior endplate. In such embodiment, the inferior endplate may define a concave bearing surface that receives the spherical bearing surface attached to the superior endplate. In yet another example of an alternative embodiment, the superior endplate, the elastic member and the dome-shaped bearing surface may be provided as a multi-durometer component formed by various molding processes, such as multi-shot injection molding, where the endplate, elastic member and bearing surface are provided as single integral part. Of course numerous other alternative embodiments are possible. Moreover, there are advantages to individual advancements described herein that may be obtained without incorporating other aspects described above. Therefore, the spirit and scope of the appended claims should not be limited to the description of the preferred embodiments contained herein.

What is claimed is:

1. An intervertebral disc prosthesis comprising:
    a) a first plate defining a receptacle;
    b) a second plate having a first bearing member that defines a convex bearing surface;
    c) an elastic member positioned within said receptacle and defining a cavity; and
    d) a second bearing member having (i) a convex mating portion positioned in mating relationship with said cavity of said elastic member, and (ii) a concave bearing surface positioned in mating relationship with said convex bearing surface so that said concave bearing surface contacts said convex bearing surface of said second plate, wherein no portion of said second bearing member contacts said first plate,
    wherein said convex bearing surface of said first bearing member of said second late is located within said receptacle of said first plate when said concave bearing surface of said second bearing member is positioned in mating relationship with said convex bearing surface.

2. The intervertebral disc prosthesis of claim 1 wherein the first plate is a superior plate and the second plate is an inferior plate.

3. The intervertebral disc prosthesis of claim 1 wherein the elastic member is comprised of an elastomer.

4. The intervertebral disc prosthesis of claim 1 wherein:
    said receptacle of said first plate is cylindrical in shape, and
    said elastomeric member includes a plurality of radially extending ribs.

5. The intervertebral disc prosthesis of claim 1 wherein:
    said receptacle of said first plate is cylindrical in shape, and
    said elastomeric member is generally cylindrical in shape.

6. The intervertebral disc prosthesis of claim 1 wherein:
    said elastic member includes a plurality of radially extending ribs, and
    said plurality of radially extending ribs define a plurality of voids, each void of said plurality of voids being interposed between a pair of adjacent ribs of said plurality of radially extending ribs.

7. The intervertebral disc prosthesis of claim 6 wherein:
    said plurality of radially extending ribs is located within said receptacle, and
    said plurality of voids is also located within said receptacle.

8. The intervertebral disc prosthesis of claim 7 wherein all of said plurality of radially extending ribs is completely located within said receptacle.

9. The intervertebral disc prosthesis of claim 8 wherein all of said plurality of voids is completely located within said receptacle.

10. The intervertebral disc prosthesis of claim 1 wherein:
    said elastic member includes (i) a first portion defining a plurality of radially extending ribs, and (ii) a second portion defining at least a partially cylindrical outer surface,
    said first plate includes (i) a receptacle sidewall that defines a receptacle opening, and (ii) a receptacle end wall that is spaced apart from said receptacle opening,
    said receptacle end wall and said receptacle side wall collectively define said receptacle,
    said first portion of said elastic member is positioned adjacent to both said receptacle end wall and said receptacle sidewall, and
    said second portion of said elastic member is positioned adjacent to said receptacle opening.

* * * * *